United States Patent [19]

Korth et al.

[11] Patent Number: 4,633,860
[45] Date of Patent: Jan. 6, 1987

[54] CANAL FORMING DEVICE FOR PERCUTANEOUS NEPHROSCOPY

[75] Inventors: Knut Korth, Merzhausen; Heinz Hluchy, Hamburg, both of Fed. Rep. of Germany

[73] Assignee: Olympus Winter & Ibe, GmbH, Hamburg, Fed. Rep. of Germany

[21] Appl. No.: 696,482

[22] Filed: Jan. 30, 1985

[30] Foreign Application Priority Data

Feb. 4, 1984 [DE] Fed. Rep. of Germany ....... 3403962

[51] Int. Cl.$^4$ ............................................. A61F 17/32
[52] U.S. Cl. .................................... 128/305; 128/751
[58] Field of Search .................... 128/303.15, 303.14, 128/305, 305.1, 305.3, 314, 4, 751, 303 R, 304; 604/22, 117

[56] References Cited

U.S. PATENT DOCUMENTS

| | | | |
|---|---|---|---|
| 864,812 | 9/1907 | Thuillier | 128/314 |
| 1,037,802 | 9/1912 | Smith | 128/314 |
| 2,001,638 | 5/1935 | Tornsjo | 604/117 |
| 2,704,541 | 3/1955 | Wyatt | 128/4 |
| 3,367,335 | 2/1968 | Ward et al. | 128/305 |
| 4,083,370 | 4/1978 | Taylor | 604/117 |
| 4,273,128 | 6/1981 | Lary | 128/344 |
| 4,444,184 | 4/1984 | Orètorp | 128/305 |

Primary Examiner—Robert Peshock
Assistant Examiner—Cary E. Stone
Attorney, Agent, or Firm—Walter C. Farley

[57] ABSTRACT

A device for preparing the insertion canal for inserting an endoscope for percutaneous nephroscopy includes a tubular member which can be guided on a guide wire inserted through the patient's skin and tissue into the renal calyx. The tubular member carries one or more scalpel blades at its distal end for creating incisions along the path of the wire which can then be expanded to provide a canal for the endoscope. Gripping, orientation and insertion depth indicating means are also disclosed.

26 Claims, 3 Drawing Figures

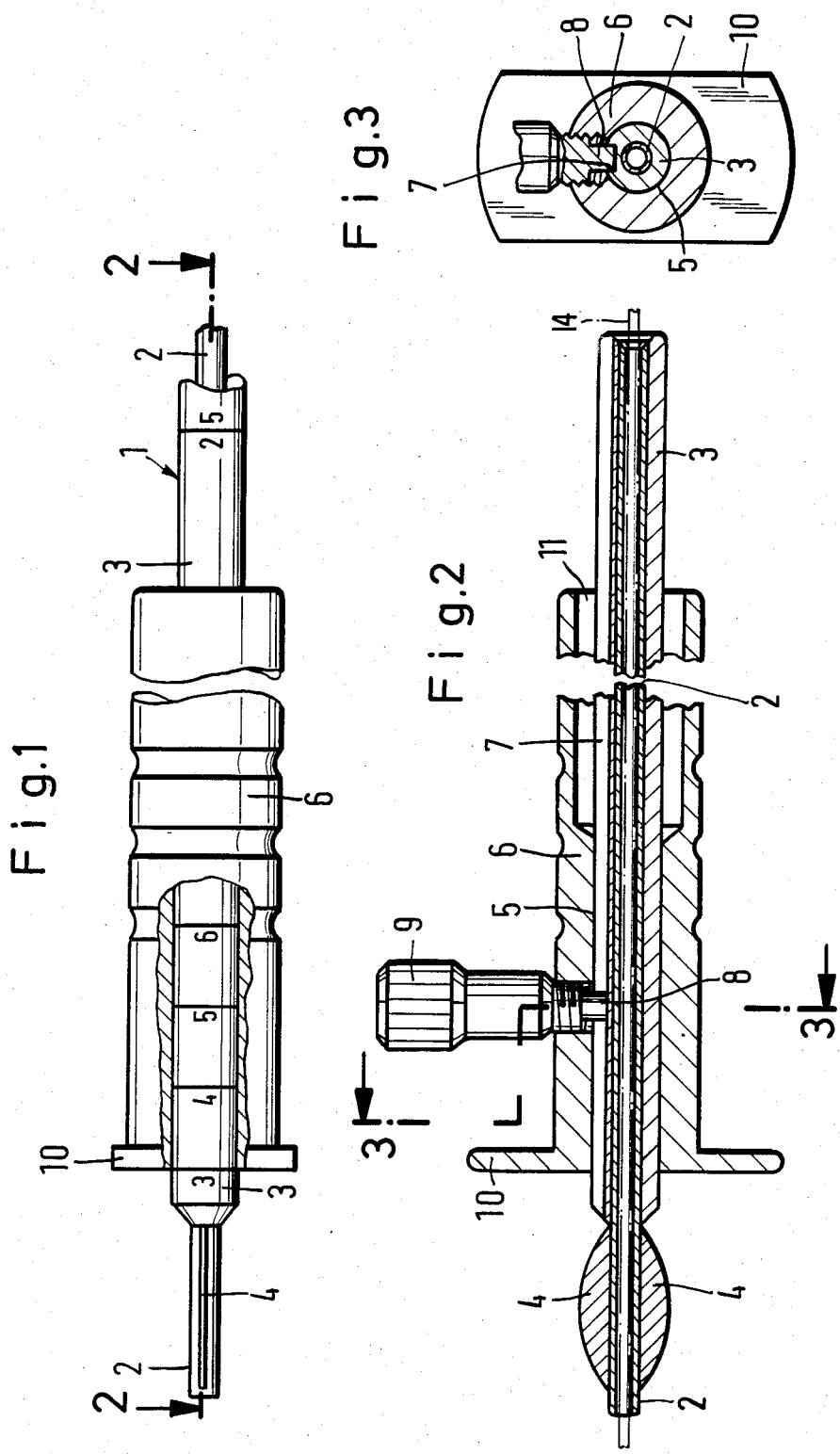

CANAL FORMING DEVICE FOR PERCUTANEOUS NEPHROSCOPY

This invention relates to an apparatus for forming a canal in the body of a patient through the skin and subcutaneous tissue to the kidney so that an endoscopic instrument can be inserted for nephroscopy.

BACKGROUND OF THE INVENTION

Percutaneous nephroscopy is being used increasingly for kidney treatment, especially for the extraction of kidney stones. Nephroscopy differs from conventional kidney surgery in that an endoscope is inserted through the skin and the tissue just beneath the skin into the kidney to perform the necessary procedure.

Before the endoscope can be inserted, an insertion canal must be created for it. This canal must be precisely positioned and must be created from the skin to the renal calyx through the tissue between the skin and the kidney as well as through the parenchyma of the kidney. A two-stage procedure is therefore used to create the canal. First, a guide wire is installed by passing it through the skin and other tissues, directing the wire with real-time observation using techniques such as X-rays and sonograms.

This kind of small-diameter canal can be formed with precision and substantially without risk. However, the passage thus formed is somewhat too small for an endoscope which can have a diameter several times larger than the wire. Thus, it is necessary to expand the canal with some form of device which can be installed on the wire, enlarging it to a size which corresponds to that of the endoscope.

In accordance with the current state of the art, dilators are used to enlarge the insertion canal by being pushed through the canal. One such dilator is described in U.S. Pat. No. 4,449,532, Storz. That device expands the canal in stages, using a series of telescopically related members of increasing diameters.

The disadvantages involved in the current state of the art arise from the process of dilating the initially narrow canal to the somewhat larger diameter of the endoscope. The initially created canal made by the wire has a diameter of perhaps 2 mm. but the endoscope may have a diameter of 10 mm., for example. This very significant expansion is the basic reason for the multiple stages of enlargement, but the technique is not totally satisfactory.

Because of the great enlargement, considerable force must be used to push the device into the patient. As a result, there is a considerable risk of undesired erroneous movements with the concomitant danger of injury. Furthermore, expansion to this extent in multiple stages requires a considerable amount of time to the discomfort of the patient. The patient particularly experiences considerable pain in procedures done under local anesthesia. Also, because of the multiple stages, the painful areas of tissue are repeatedly irritated.

Problems also arise at certain tissue points such as, for example, at hard, difficult-to-penetrate muscle tissue, at hardened muscles or when scar tissue from previous surgery is required to stretch.

SUMMARY OF THE INVENTION

An objective of the present invention is to provide a device which allows and facilitates rapid formation and enlargement of an insertion canal for an endoscope which is relatively pain-free for the patient and which requires less force on the part of the surgeon.

Briefly described, the invention comprises an apparatus for preparing a canal for the insertion of an endoscope into a patient for percutaneous nephroscopy along a path defined by a small-diameter guide wire inserted into the renal calyx. An elongated, thin-walled hollow tube having an inner diameter slightly larger than the guide wire is provided with an axially extending scalpel blade fixedly attached to the distal end of the tube, the blade protruding radially from the outer surface of the tube. The tube can be slidably moved along the guide wire into the patient so that the scalpel blade creates an incision along the path of the wire.

BRIEF DESCRIPTION OF THE DRAWINGS

In order that the manner in which the foregoing and other objects are attained in accordance with the invention can be understood in detail, a particularly advantageous embodiment thereof will be described with reference to the accompanying drawings, which form a part of this specification, and wherein:

FIG. 1 is a foreshortened top plan view of an apparatus in accordance with the invention;

FIG. 2 is a foreshortened side elevation, partly in section, along line 2—2 of FIG. 1; and FIG. 3 is a transverse sectional view along line 3—3 of FIG. 2.

DETAILED DESCRIPTION OF THE PREFERRED EMBODIMENT

As shown in the figures, the apparatus comprises an instrument 1 with a shaft 3 surrounding an elongated, relatively thin-walled tube 2, shaft 3 being fixed to tube 2 in a concentric relationship. The shaft has a somewhat larger outer diameter than the tube. At the distal end of the instrument, i.e., the end which will be distal relative to the surgeon and which will be inserted into the patient, the tube protrudes from the shaft. This is illustrated at the left in FIGS. 1 and 2.

A scalpel blade 4 is located at the distal end of tube 2 adjacent the distal end of shaft 3. In the embodiment shown, the scalpel blade arrangement includes two scalpel blades positioned symmetrically on tube 2, the blades lying in a plane containing the axes of tube 2 and shaft 3. It will also be observed that the distal end of shaft 3 has a tapered conical shape leading to a small-diameter end.

The scalpel blades 4 are attached in any convenient way to tube 2 in the plane of the tube axis. The two blades are symmetrically shaped with arcuate, axially extending cutting edges so as to be capable of cutting in either axial direction of movement, during insertion or withdrawal.

The outer surface of shaft 3 is provided with indicia, illustrated in part in FIG. 1, for the purpose of indicating the degree of insertion of the instrument as will be further described. The specific markings shown are 3, 4, 5, 6 and 25 which can represent decimeters or any other desired measure or which can be arbitrary markings for the surgeon's reference.

A handle or grip device 6 having a longitudinal bore 5 surrounds shaft 3 so that the instrument 1 can be more easily handled. A longitudinal groove or slot 7 is formed in shaft 3 and a pin 8 extends into slot 7. Pin 8 is mounted on a knob 9 which is supported in handle 6 and which can be rotated to adjust the degree to which pin 8 extends into slot 7. The axes of pin 8 and knob 9 are perpendicular to the axis of instrument 1. The knob and pin arrangement serves to attach handle 6 to the assembly including tube 2 and shaft 3 and also prevents rotation of handle 6 relative to shaft 3. In addition, it will be noted that handle 6 is slidable along shaft 3. Pin 8 can be tightened into slot 7 to fix the position of the handle at any location along shaft 3.

A stop plate 10 is integrally formed at the distally facing end of handle 6. As seen in FIG. 3, the stop plate has an elongated, generally rectangular shape with its longer dimension being parallel with the plane containing the scalpel blades and also with the central plane of groove 7. Thus, plate 10 constantly indicates the position of the scalpel blades and can be observed by the surgeon as the procedure progresses.

Handle 6 advantageously is made from a lightweight material such as aluminum and is made even lighter by the formation of an axial recess 11. This results in a lightweight, easily handled instrument.

The process of using the instrument 1 begins with the determination of the distance between the skin surface and the renal calyx using some technique such as X-rays or sonograms. The insertion depth is then set on the instrument itself by loosening knob 9 and sliding the handle relative to the shaft until the proper distance exists between the end of tube 2 and stop plate 10. The instrument is then ready for use. A guide wire 14 is inserted into the calyx in a known manner and the instrument 1 is slid along the wire with the wire passing along within the interior of tube 2. The wire and tube are chosen so that a snug, sliding relationship exists betwen them. The scalpel blades are then pushed into the skin and through the tissues until the stop plate 10 rests against the patient's skin. This forms an incision up to a point just before the kidney. The apparatus of the invention is then removed and, if desired, is turned through an angle of 90 degrees so that a second, perpendicular incision can be formed with a second insertion. The insertion canal thus formed can then be dilated and the endoscope inserted.

The device described can be varied in various ways within the scope of the invention. For example, the shape of the scalpel blades can be chosen to be different, triangular for example, and for special cases a scalpel with nonsymmetrical blades can be chosen or a blade can be used on only one side of shaft 3.

The shaft 3 can have a uniform diameter throughout its length. However, the illustrated shape in which the shaft has a very small end adjacent the scalpel blades is preferred particularly so that the instrument can be inserted into the initially rather small opening. The shaft portion which is proximal from the scalpel should, however, be designed as a strong, reinforced piece. This can be accomplished by forming the arrangement which is depicted as two tubes as a single, integral piece so that the more proximal region is relatively rigid and sturdy, the distal region still being small.

The stop plate 10 can be formed separately from the handle and can be attached to the shaft 3 in spaced relationship with the handle in which case only the stop plate and not the entire handle can be adjustable. However, it is preferable to have the relationship shown in which the handle is as far toward the distal end as is convenient and as close to the stop plate as possible. It is possible, of course, to omit the stop plate and handle completely but it is not desirable.

The arrangement of the blades can also be varied from that shown by using four blades separated by angles of 90 degrees so that the previously described criss-cross incision can be achieved with one insertion. Other configurations such as one in which the blades are separated by angles of 120 degrees are also possible.

In some cases a spiral incision may be of interest for which the blade planes are adjusted to differ by a slight angle from the plane containing the tube and shaft axes.

While certain advantageous embodiments have been chosen to illustrate the invention it will be recognized by those skilled in the art that various changes and modifications can be made therein without departing from the scope of the invention as defined in the appended claims.

What is claimed is:

1. An apparatus for preparing a canal for insertion of an endoscope into a patient for percutaneous nephroscopy along a path defined by a small diameter guide wire inserted percutaneously into the renal calyx comprising the combination of
    an elongated hollow tube having an inner diameter slightly larger than the diameter of the guide wire; and
    an axially extending scalpel blade fixedly attached to the distal end of said tube and protruding radially from the outer surface thereof,
    whereby said tube can be slidably moved along said guide wire into the patient so that said scalpel blade creates an incision adjacent to the path of said wire.

2. An apparatus according to claim 1 and including two radially extending scalpel blades on opposite sides of said tube, said blades being axially symmetrical.

3. An apparatus according to claim 2 wherein the cutting edges of said blades are formed so that said edges are capable of cutting in either axial direction of movement.

4. An apparatus according to claim 3 wherein each of said blades has a cutting edge which is arcuate in an axial plane.

5. An apparatus according to claim 2 and further comprising a tubular shaft portion fixedly attached to and coaxially surrounding said tube and extending from said scalpel blades toward the proximal end of said tube, said shaft portion having a significantly larger diameter than said tube.

6. An apparatus according to claim 5 and further comprising a grip member and a stop plate mounted on said shaft portion, said grip member and stop plate being axially movable along said shaft portion toward and away from said scalpel blades, said grip member including means for indicating the mounting angle of said blades.

7. An apparatus according to claim 6 wherein said shaft portion includes a longitudinal groove and said grip member includes a key member riding in said groove to prevent relative rotation between said shaft portion and said grip member and stop plate.

8. An apparatus according to claim 7 wherein the outside width of said scalpel blades is smaller than half the diameter of the endoscope to be used.

9. An apparatus according to claim 2 wherein the outside width of said scalpel blades is smaller than half the diameter of the endoscope to be used.

10. An apparatus according to claim 1 wherein the cutting edge of said blade is formed so that it is capable of cutting in either axial direction of movement.

11. An apparatus according to claim 1 and further comprising a tubular shaft fixedly attached to and coaxially surrounding said tube and extending from said scalpel blade toward the proximal end of said tube, said shaft having a significantly larger diameter than said tube.

12. An apparatus according to claim 11 wherein said shaft includes a tapered portion tapering outwardly from said scalpel blade toward the proximal end thereof.

13. An apparatus according to claim 12 and further comprising a grip member mounted on said shaft, said grip member being axially movable along said shaft toward and away from said scalpel blade.

14. An apparatus according to claim 13 and including a stop plate adjustably mounted on said shaft.

15. An apparatus according to claim 14 wherein said shaft carries indicia for indicating the distance between said stop plate and said scalpel blade.

16. An apparatus according to claim 11 and including a stop plate adjustably mounted on said shaft.

17. An apparatus according to claim 16 and further including two radially extending scalpel blades on opposite sides of said tube, said blades being axially symmetrical.

18. An apparatus according to claim 17 wherein the cutting edges of said blades are formed so that they are capable of cutting in either axial direction of movement.

19. An apparatus according to claim 18 wherein each of said blades has a cutting edge which is arcuate in the axial direction.

20. An apparatus according to claim 1 and further comprising a grip member mounted on said tube, said grip member being axially movable along said tube toward and away from said scalpel blade.

21. An apparatus according to claim 20 wherein the outside width of said scalpel blades is smaller than half the diameter of the endoscope to be used.

22. An apparatus according to claim 1 and including a stop plate adjustably mounted on said tube.

23. An apparatus according to claim 22 wherein said tube carries indicia for indicating the distance between said stop plate and said scalpel blade.

24. An apparatus according to claim 22 and further comprising a grip member mounted on said tube with said stop plate, said grip member including means for indicating the mounting angle of said blades.

25. An apparatus according to claim 1 wherein said tube includes a concentric, integral shaft portion, said distal end of said tube carrying said scalpel blade having a small diameter and said shaft portion having a larger diameter.

26. An apparatus according to claim 1 wherein the outside width of said scalpel blades is smaller than half the diameter of the endoscope to be used.

* * * * *